US010653336B2

(12) United States Patent
Mo et al.

(10) Patent No.: US 10,653,336 B2
(45) Date of Patent: May 19, 2020

(54) SUBCUTANEOUSLY IMPLANTABLE SENSOR DEVICES AND ASSOCIATED SYSTEMS AND METHODS (71) Applicant: Intel Corporation, Santa Clara, CA (US)

(72) Inventors: Stanley Mo, Hillsboro, OR (US); Alexandra Zafiroglu, Portland, OR (US); Giuseppe Raffa, Portland, OR (US); Joshua Ratcliff, San Jose, CA (US); Jose Sia, Hillsboro, OR (US); Adam Jordan, El Cerrito, CA (US)

(73) Assignee: Intel Corporation, Santa Clara, CA (US)

( * ) Notice: Subject to any disclaimer, the term of this patent is extended or adjusted under 35 U.S.C. 154(b) by 325 days.

(21) Appl. No.: 15/590,969

(22) Filed: May 9, 2017

(65) Prior Publication Data
US 2018/0085029 A1    Mar. 29, 2018

Related U.S. Application Data (63) Continuation of application No. 14/317,221, filed on Jun. 27, 2014, now Pat. No. 9,642,556.

(51) Int. Cl.
A61B 5/1455    (2006.01)
A61B 5/07      (2006.01)
A61B 5/00      (2006.01)
A61B 5/145     (2006.01)

(52) U.S. Cl.
CPC ............ A61B 5/076 (2013.01); A61B 5/0031 (2013.01); A61B 5/14503 (2013.01); A61B 5/4839 (2013.01); A61B 5/4848 (2013.01); A61B 5/686 (2013.01); A61B 5/14532 (2013.01)

(58) Field of Classification Search
CPC ..... A61B 5/0002; A61B 5/0031; A61B 5/145; A61B 5/14503; A61B 5/14507; A61B 5/14532; A61B 5/14539; A61B 5/1455; A61B 5/1459; A61B 5/1468;
(Continued)

(56) References Cited

U.S. PATENT DOCUMENTS 4,694,572 A * 9/1987 Leber ................ H05K 1/095
                                            174/257
5,556,421 A   9/1996 Prutchi et al.
5,833,603 A  11/1998 Kovacs et al.
(Continued)

FOREIGN PATENT DOCUMENTS

CN    102481110 A    5/2012
JP    2000500380 A   1/2000
(Continued)

OTHER PUBLICATIONS

Office Action dated Jul. 10, 2018 for Japanese Patent Application No. JP2017-515002, 16 pages.
(Continued)

Primary Examiner — Eric F Winakur
(74) Attorney, Agent, or Firm — Schwabe, Williamson & Wyatt, P.C.

(57)    ABSTRACT

Methods of using subcutaneously implantable sensor devices and associated systems having a communication module that is controlled based upon the detection of a predetermined chemical agent.

13 Claims, 3 Drawing Sheets (58) Field of Classification Search
CPC ... A61B 5/1486; A61B 5/6846; A61B 5/6847; A61B 5/686; A61B 5/7282; A61B 5/74
See application file for complete search history.

(56) References Cited

U.S. PATENT DOCUMENTS

| | | |
|---|---|---|
| 6,208,894 B1 | 3/2001 | Schulman et al. |
| 7,484,129 B1 | 1/2009 | Varrichio et al. |
| 8,216,130 B2 | 7/2012 | Glukhovsky et al. |
| 2007/0049252 A1 | 3/2007 | Smith et al. |
| 2008/0021519 A1 | 1/2008 | De Geest et al. |
| 2008/0071328 A1 | 3/2008 | Haubrich et al. |
| 2008/0262331 A1 | 10/2008 | Gerber et al. |
| 2009/0085768 A1 | 4/2009 | Patel et al. |
| 2010/0115279 A1 | 5/2010 | Frikart et al. |
| 2012/0018302 A1 | 1/2012 | Shiraki et al. |
| 2012/0190989 A1 | 7/2012 | Kaiser et al. |
| 2012/0283540 A1 | 11/2012 | Brüggemann |
| 2012/0296189 A1 | 11/2012 | Bhogal et al. |
| 2013/0076531 A1 | 3/2013 | San Vicente et al. |

FOREIGN PATENT DOCUMENTS

| | | |
|---|---|---|
| JP | 2003-533318 A | 11/2003 |
| JP | 2004533302 A | 11/2004 |
| JP | 2010540181 A | 12/2010 |
| WO | WO2013/177573 A2 | 11/2013 |
| WO | 2014043649 A1 | 3/2014 |
| WO | WO2015/072114 A1 | 5/2015 |

OTHER PUBLICATIONS

Non-Final Office Action dated Nov. 6, 2015 for U.S. Appl. No. 14/317,221, 6 pages.
Final Office Action dated Apr. 22, 2016 for U.S. Appl. No. 14/317,221, 6 pages.
Non-Final Office Action dated Aug. 26, 2016 for U.S. Appl. No. 14/317,221, 7 pages.
Notice of Allowance dated Jan. 3, 2017 for U.S. Appl. No. 14/317,221, 5 pages.
International Search Report and Written Opinion dated Aug. 26, 2015 for PCT/US2015/032660, 20 pages.
International Preliminary Report on Patentability dated Jan. 5, 2017 for PCT/US2015/032660, 16 pages.
Office Action and Search Report dated Aug. 10, 2016 for Taiwan Application No. 104116073, 12 pages.
Office Action dated Nov. 7, 2017 for Japanese Application No. 2017-515002, 27 pages.
Office Action dated Mar. 12, 2019 for Japanese Patent Application No. JP2017-515002, 15 pages.
Office Action dated May 15, 2019 for Chinese Patent Application No. 201580027733.7, 10 pages.
Office Action dated Oct. 8, 2019 for Chinese Patent Application No. 201580027733.7, 11 pages.
Office Action dated Sep. 10, 2019 for Japanese Patent Application No. JP2017-515002, 15 pages.

* cited by examiner

SUBCUTANEOUSLY IMPLANTABLE SENSOR DEVICES AND ASSOCIATED SYSTEMS AND METHODS

PRIORITY DATA

This application is a continuation of U.S. patent application Ser. No. 14/317,221, filed on Jun. 27, 2014, now issued as U.S. Pat. No. 9,642,556, which is incorporated herein by reference.

BACKGROUND

Chemical sensors generally perform at least two basic functions. First, chemical sensors recognize or detect various aspects of a test sample. Second, chemical sensors transduce the information they obtain to a user. Chemical sensors can have a broad range of applications, some of which include the areas of environmental monitoring, military defense, healthcare, and biotechnology. Subcutaneously implantable sensors can be especially useful in recognizing occurrences inside the body. As is the case with all health-related information, the data collected by subcutaneously implantable chemical sensors is typically personal and confidential.

DESCRIPTION OF EMBODIMENTS

Although the following detailed description contains many specifics for the purpose of illustration, a person of ordinary skill in the art will appreciate that many variations and alterations to the following details can be made and are considered to be included herein. Accordingly, the following embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

As used in this specification and the appended claims, the singular forms "a," "an" and "the" include plural referents unless the context clearly dictates otherwise. Thus, for example, reference to "a sensor" includes a plurality of such sensors.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term, like "comprising" or "including," it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein. The term "coupled," as used herein, is defined as directly or indirectly connected in an electrical or nonelectrical manner. Objects described herein as being "adjacent to" each other may be in physical contact with each other, in close proximity to each other, or in the same general region or area as each other, as appropriate for the context in which the phrase is used. Occurrences of the phrase "in one embodiment," or "in one aspect," herein do not necessarily all refer to the same embodiment or aspect.

As used herein, a "predetermined chemical agent" refers to a chemical or biological agent that a subcutaneously implantable sensor is programmed to recognize. Any number of molecules, proteins, peptides, amino acids, antibodies, enzymes, metabolites, or compounds can be identified as a "predetermined chemical agent."

As used herein, an "analyte" refers to any chemical or biological agent for which analysis is sought. Predetermined chemical agents of the type herein listed as well as others not listed can be considered analytes in a context where such is the target chemical or agent to be detected and/or monitored by the subcutaneously implantable sensor device.

As used herein an "adverse chemical agent" refers to an agent, or an amount of an agent that is considered undesirable or biologically harmful. Examples include poisons, toxins, radioactive particles, heavy metals (in certain amounts) or other inorganic elements or compounds considered to be hazardous to a subject's health.

As used herein a "therapeutic agent" refers to an agent that can have a beneficial or positive effect on a subject when administered to the subject in an appropriate or effective amount.

As used herein, a "subject" refers to an animal. In one aspect the animal may be a mammal. In another aspect, the mammal may be a human.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 angstroms to about 80 angstroms" should also be understood to provide support for the range of "50 angstroms to 80 angstroms." Furthermore, it is to be understood that in this specification support for actual numerical values is provided even when the term "about" is used therewith. For example, the recitation of "about" 30 should be construed as not only providing support for values a little above and a little below 30, but also for the actual numerical value of 30 as well.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

Reference in this specification may be made to devices, structures, systems, or methods that provide "improved" performance. It is to be understood that unless otherwise stated, such "improvement" is a measure of a benefit obtained based on a comparison to devices, structures, systems or methods in the prior art. Furthermore, it is to be understood that the degree of improved performance may vary between disclosed embodiments and that no equality or consistency in the amount, degree, or realization of improved performance is to be assumed as universally applicable.

Example Embodiments

An initial overview of invention embodiments is provided below and specific embodiments are then described in further detail. This initial summary is intended to aid readers in understanding the technological concepts more quickly, but is not intended to identify key or essential features thereof, nor is it intended to limit the scope of the claimed subject matter.

One issue hindering widespread acceptance and use of subcutaneously implantable sensors is the need for power in their operation. Because the sensor is implanted under the skin of a subject, it is generally not accessible for maintenance, including battery or power cell replacement. Another issue is the challenge of accessing data that is gathered by the sensor. One solution to these issues is the use of a line extending from the sensor and out through the subject's skin which allows wired access to the sensor. Such a line can be used both to charge the sensor's power supply and to access information gathered by the sensor. However, the extension of such a line through the skin presents a number of significant disadvantages, such as pain, inconvenience, risk of infection, risk of injury, need for ongoing care, etc.

One solution to the issue of data retrieval can be to communicate with the sensor wirelessly. This can be accomplished by including a wireless transmitter/receiver in the sensor. While convenient in many respects, the power demands of a continuously operated wireless transmitter/receiver only further add to the already existing issues in powering the sensor for its intended operational duration. An implantable sensor device that is completely self-contained and is capable of being implanted in a subject and remaining fully functional over an extended duration without the need for any physical interaction is highly desirable.

Invention embodiments set forth herein provide subcutaneously implantable sensors devices and related systems and methods that can collect and wirelessly report data with minimal power requirements. Such a device can have a number of basic components including without limitation, a housing, at least one sensor (such as a chemical sensor), a power module, a data collection module, a communication module, and a controller module. Each of these components is discussed in further detail below.

Figure 1:
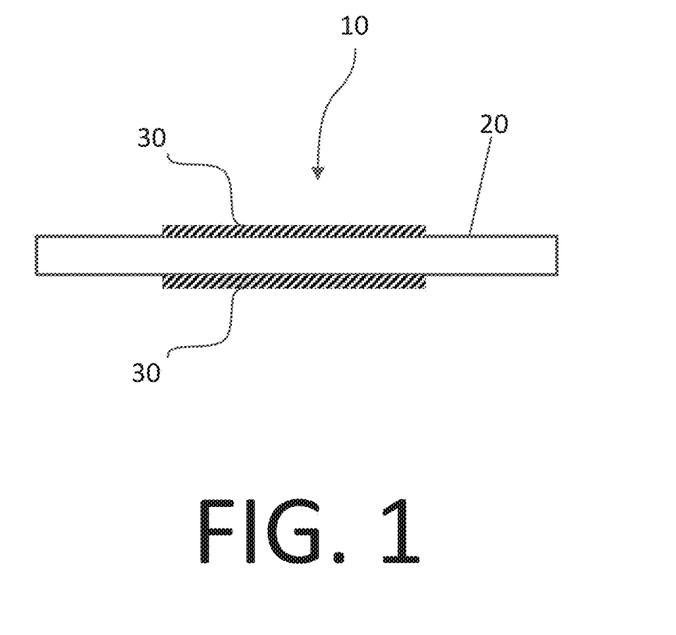
FIG. 1 is a profile view of a subcutaneously implantable sensor device with a sensor on each of two substantially opposing sides in accordance with an invention embodiment.

Referring to FIG. 1 is shown a profile view of one embodiment of a subcutaneously implantable sensor device 10 having a housing 20 and sensors 30 positioned on opposing sides of the housing. Additional components resident within the housing (not shown) are a power module, a data collection module, a communication module, and a controller module. The housing can be adapted to protect various components of the sensor device from bodily fluids and provide a support structure for the sensor or sensors as the case may be. The housing can be made of any material known in the art that is suitable to minimize biofouling, implant rejection, or other adverse effects generally related to implantation of devices within the body of a subject. Example of materials include without limitation, corrosion free metals, such as stainless steel, nickel, chromium, silver, gold and alloys thereof, and polymeric materials such as polyurethane, polyethylene, polypropylene, and the like. Additionally composite materials and nearly any other material that is biologically safe, corrosion resistant, and capable of functioning as a suitable barrier between a biological environment and the internal sensor components can be used.

Regarding the specific shape, design, and dimension of the housing, nearly any shape, design, or size can be used which is suitable to achieve a desired purpose. For example, while depicted in FIG. 1 with corners, the housing shape may be rounded, oval, oblong, spherical, etc. and may have a desired rigidity (i.e. can be hard or soft). Such shape and size considerations may be specified based on the intended purpose or placement within a subject.

Figure 2:
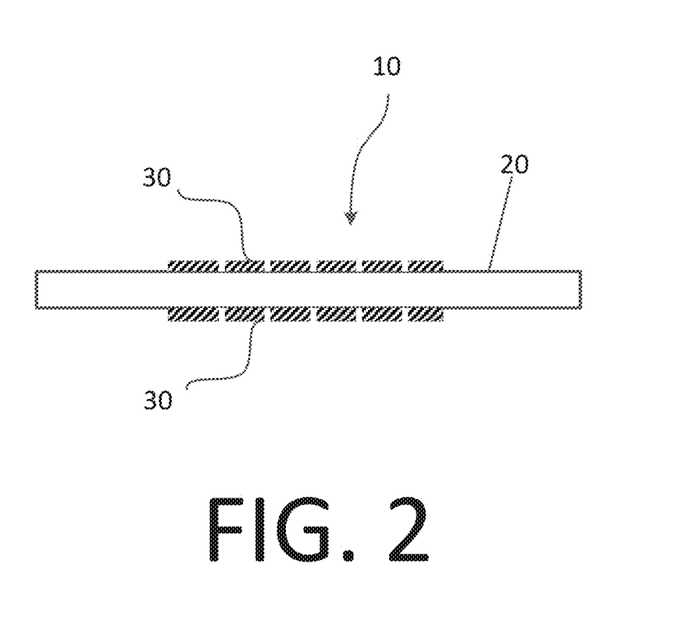
FIG. 2 is a profile view of a subcutaneously implantable sensor device with a sensor array on each of two substantially opposing sides in accordance with an invention embodiment.

Any suitable sensor, including chemical sensors, may be used with the present technology and can be selected based on the intended sensing to be performed. Exemplary sensors include without limitation, electrochemical, potentiometric, amperometric, conductometric, chemicapacitive, chemiresistive, photoionizing, a field-effect transistor, a physical transducer, an optical transducer, biochemical, affinity-based, thermochemical, optical, piezoelectric, or any other suitable sensor. The chemical sensor can have a single recognition site or a plurality of recognition sites depending on the degree of sensitivity desired in the sensor. The plurality of recognition sites can be configured to detect a plurality of agents. For example, in the case of an affinity-based chemical sensor designed to detect a specific class of analytes, various recognition sites could have modified functionality in order to increase their affinity for a specific segment of that class of analytes to ensure adequate detection across the entire class. As shown in FIG. 2, as an alternative to a sensor with a plurality of recognitions sites, an array of sensors may be used which are configured to detect different agents.

In certain embodiments, an implantable sensor device may have at least one sensor. As depicted in FIGS. 1 and 2, the device 10 has two sensors 30, or two sensor arrays, and such sensors are upon generally opposing sides of the housing 20. Such a configuration can be advantageous in some aspects as in order to receive sensory input from different directions in the body. For example, when placed within or just under the dermal layer, one side of the implantable sensor device may be oriented toward the dermal layer with the other side oriented toward the circulatory system. In such orientation, the implantable sensor device can receive sensory input from both. In some embodiments the implantable sensor devices can have any number of sensors desired. In one embodiment, the device may have from 1-100 sensors.

In some embodiments, the sensors may be configured to detect specific predetermined chemical agents. In another embodiment, the sensors may be configured to detect a specific analyte of interest. Detection of either of these can be on a presence or absence basis or on a concentration basis. In other words, in some embodiments, the sensors may be configured to detect either the presence or absence of a given agent. In other embodiments, the sensors may be configured to detect the concentration or amount of a given chemical agent. In yet other embodiments, the sensors can be configured to detect presence or absence as well as concentration or amount of a given agent.

Figure 3:
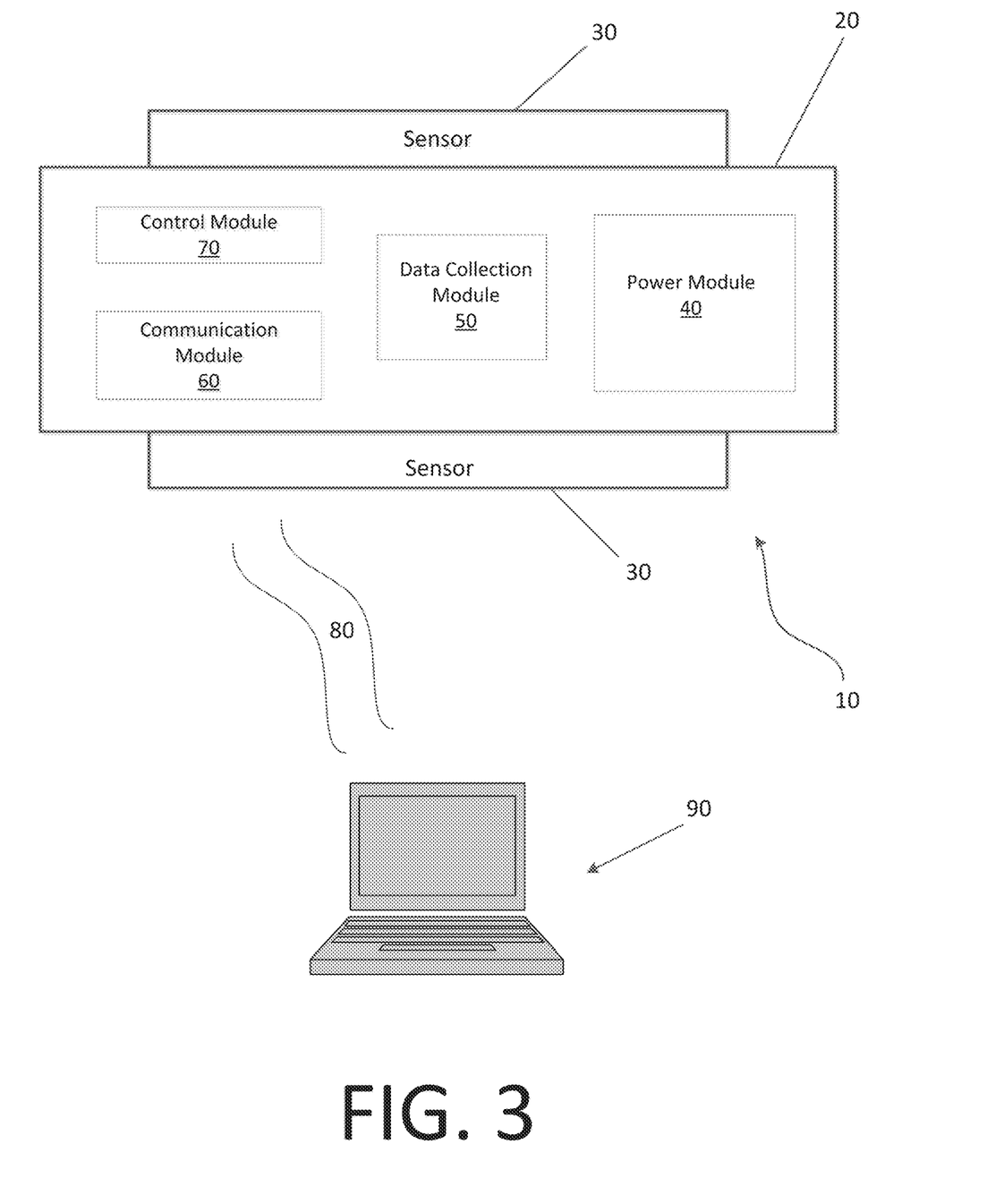
FIG. 3 is a schematic view of a subcutaneously implantable sensor device in accordance with an invention embodiment.

Referring to FIG. 3 is shown a schematic view of an implantable sensor device 10 in accordance with an invention embodiment. In addition to the housing 20 and the sensor(s) 30 as previously discussed, the device may include a number of other modules or components in order to carry out its intended operation. At a basic level, such components include a power module 40, a data collection module 50, a communication module 60, and a controller module 70.

The power module 40 is configured to power the sensor device 10. Any power source sufficient to adequately power the implantable sensor device may be used. Batteries, capacitors, and/or other power sources may be selected in view of the device's intended purpose and duration of operation. In one aspect, the power module can include a battery. In one example the battery can be a rechargeable battery. Other components (not shown) can be included in the power module 40, for example, wires and electrical connections required to operably connect the battery to other modules within the implantable sensor device 10 that require power for their operation. In one specific example, the power module may include components that inductively charge the battery when exposed to an adequate external influence, such as a wireless or magnetic influence. In such embodiment, if charging of the battery is necessary or desired, the proper external influence can be brought within a sufficient range to operate the inductive components and charge the battery without physically accessing the implantable sensor device.

The data collection module 50 is operatively coupled to the sensor(s) 20 in a manner sufficient to receive sensor data, and is configured to collect and store sensor data. Typical components of a data store may be used, such as readable writable memory, connections to power, and suitable input/output (I/O) connections to other device components or modules. Those of ordinary skill in the art will understand the assembly and operation of such components.

The communication module 60 is configured to communicate with a remote device 90, such as a computing device (i.e. computer), mobile device (e.g. smart phone or tablet), or cloud database, in order to transmit and/or receive information. Typical components for such a module may be used. In one aspect, the communication module may include a wireless transmitter/receiver capable of wirelessly communicating 80 with the remote device 90. Nearly any wireless frequency, range, protocol or type can be used, for example short-wavelength radio waves in various bands, such as Bluetooth®, local area wireless technologies, such as WiFi, WiMAX®, or other IEEE 802.11 protocols, cellular, including GMA and CDNA, radio, electromagnetic, or any other suitable method of wireless communication. In one embodiment, the wireless transmitter/receiver can be a low power consumption device, for example, Bluetooth® low energy (LE).

The controller module 70 is configured to control the operation of the implantable sensor device 10, including all aspects of sensor activity, data collection, and communications. The controller module is operatively coupled to the other device modules as necessary to affect such control. The controller module generally includes one or more processors and memory and is equipped with program logic sufficient to control all aspects and function of the device.

In one embodiment, the program logic of the controller may include instructions to control the communications module 60 based on sensor activity. For example, the controller module 70 can activate or deactivate the communication module 60 and/or other device components upon receiving an indication of the amount, presence, or absence of a predetermined chemical agent by the sensor(s) 30. In one aspect, the controller can activate the communications module 60 upon detection of a predetermined chemical agent by the sensor(s) 30. In another aspect, the controller can deactivate the communications module 60 upon the sensor(s) 30 detecting the absence of a predetermined chemical agent. In a further aspect, the controller can activate the communications module 60 upon detection by the sensor(s) 30 of a predetermined chemical agent in an amount above a specified concentration. In yet another aspect, the controller can deactivate the communications module 60 upon sensor(s) 30 detection of a predetermined chemical agent in an amount below a specified concentration. In an additional aspect, deactivation of the communications module 60 can occur based on an amount of time that has lapsed since its activation. Such an amount of time can be programmed into the controller as part of the program logic and selected by a user in view of the desired purpose and operation of the sensor device.

In some embodiments, the sensor(s) 30 can be configured to detect a predetermined chemical agent, an analyte of interest, or both. In some embodiments, as previously mentioned, an array of sensors (as shown in FIG. 2) can be used with some sensors in the array configured to detect a predetermined chemical agent while others are configured to detect an analyte of interest. In some embodiments, the sensor array may be configured to detect multiple analytes and optionally the predetermined chemical agent. In some embodiments each segment of the array can be configured to detect a single agent (i.e. predetermined chemical agent or analyte). In other embodiments, each array segment can be configured to detect multiple agents. The predetermined chemical agent can be either endogenous or exogenous. In situations where the predetermined chemical agent is endogenous, it can in some embodiments, also be an analyte of interest.

The remote device 90 can be any number of computing devices that are capable of wirelessly communicating with the sensor device 10. As previously mentioned, exemplary devices include without limitation desktop computers, mobile devices, such as smart phones and tablets and cloud databases. In addition to a wireless transmitter/receiver, such devices may also include processors, memory, and I/O components necessary for a user to operate the device, among others. Generally, components sufficient to report data received by the remote device to the user can be included. Such computing devices are well known in the art. In one aspect, the remote device can be equipped with an application that is configured to display, quantify, and interpret data received from the implantable sensor device. In some aspects, the remote device and/or the program logic thereon can control, program, or otherwise input information into the subcutaneously implantable sensor.

In an additional embodiment, the remote device can be wirelessly connected to a second remote device. In some aspects, the second remote device can have all standard parts for a computing device and in some embodiments may also include other machinery and components configured for carrying out a physical task. One example of such a task may be administering an agent to the subject in which the implantable sensor device is implanted. In some aspects, the remote device itself may be equipped with such components. Examples of such components include without limitation, reservoirs, pumps, lines, needles, read outs, etc. In one embodiment, the remote device, or second remote device can be an insulin pump or other device for parenterally administering an agent to the subject. Another example may be a device for administering epinephrine or other agent in order to counteract, prevent, reverse, or treat, physiological activities detected, or adverse chemical agents or analytes detected. In one embodiment, the implantable sensor device may be configured to include such components for dispensing or releasing an agent in response to a stimulus detected by the sensor(s). Again, such components may include an active agent to be released or dispensed, a reservoir for holding such, and a release mechanism for releasing such. Further, such components would be operatively coupled to the controller module and the controller module equip with program logic sufficient to direct release of the active agent upon detection of the physiologic activity, adverse chemical agent, or analyte. Examples of physiologic activity may include commencement of anaphylaxis, cardiac arrhythmia or arrest, increase or decrease in blood pressure, or an increase in specific proteins, enzymes, or antibodies. In one embodiment, examples of an adverse chemical agent can include any toxic or poisonous substance, or a specific threshold amount or concentration of a substance that is indicated as toxic above a specified level.

For example, the implantable sensor device could be used to monitor the occurrence of a biological condition that is accompanied by a specific analyte or chemically induced signal that is detectable by the sensor device. Upon detection of this signal, the communication module can be activated and transmit the sensor data to a user, such as the individual in which the sensor device has been implanted, a medical professional, or other designated person. Alternatively, a chemical agent or chemically induced signal could be delivered to the person in whom the sensor device is implanted in order to monitor the data that has been collected and stored by the device. In this aspect of the embodiment it can be particularly useful to have an array of different types of sensors. The sensor device can have an array of various sensors that monitor conditions inside the body and at least one sensor that detects the predetermined chemical agent in order to activate the communication module and transmit the collected data to a remote device for immediate evaluation or storage in a database. In one aspect of this embodiment, the sensor device is configured to detect at least one of the presence, absence, and concentration of an analyte, where the analyte can be the predetermined chemical agent or a different analyte. Hence, the controller module can activate the communication module based on either the detection of the predetermined chemical agent, a different analyte, or both.

In a further embodiment of the invention, the subcutaneously implantable sensor device may include a signaling component (not shown). Such a component can produce a signal, such as a biofeedback signal, upon detection of a predetermined chemical agent or analyte. A number of signal types and mechanisms can be used including without limitation, a vibrator to produce vibrations, an electrode to provide an electrical signal (i.e. shock), an audio device to produce an auditory signal, a heat device to produce a thermal signal, and/or an optical device to produce a visual signal. Additionally, the sensor device may release chemicals, or cause the subject's body to release chemicals in response to the sensory data received. The signal type and mechanism can be selected in accordance with the intended placement and function of the implantable sensor device.

When an implantable sensor device is used in connection with a remote device wirelessly communicating therewith, a powerful biological data sensing and reporting system for monitoring events within a subject's body is created. Such a system has wide-sweeping applications across multiple industry sectors, such as health and safety, medicine and pharmaceutics, and sports among others. When the remote device, or second remote device, is equipped to perform a function beyond merely receiving and analyzing sensory data, systems are created which can further treat or prevent physiologic conditions.

In operation, the above-recited devices and systems are capable of performing a number of useful methods. In one embodiment a method of controlling communication activity of a subcutaneously implantable sensor device is provided. Such a method may include identifying a predetermined chemical agent to be detected by a sensor, and activating a communications module of the subcutaneously implantable sensor device in response to detection of the predetermined chemical agent by the sensor. In some aspects, such a method can further include programming a controller module of the sensor device with logic that controls operation of a communication module of the sensor device based upon, or in response to, detection of a predetermined chemical agent or signal (including electrical or pressure signals) by at least one sensor of the sensor device.

Once activated, the communications module can communicate with a remote device. During communication, information can be sent from the implantable sensor device to the remote device, from the remote device to the sensor device, or exchanged between both devices. In one embodiment, information obtained by the implantable sensor device, including information obtained since its last communication with the remote device can be sent to the remote device. In one embodiment, the information may be information that was collected and stored in the data collection module. Alternatively, in another embodiment, the information can be information that is sent from the remote device to the implantable sensor device. For example, information regarding the operation and function of the implantable sensor device, commands affecting the memory in the data collection module (such as wiping or clearing it), etc. may be sent from the remote device to the implantable sensor device. In effect, nearly any piece or type of information can be conveyed or exchanged between the two devices when they are in communication with one another. Following the completion of the data or information exchange, the communications module of the subcutaneously implantable sensor can be deactivated or turned off and the communication session terminated. In one aspect of this embodiment, deactivation of the communication module minimizes power usage of the sensor device. This method of controlling communication activity can reduce or minimize power usage by the implantable sensor device. As such, in an invention embodiment a method of reducing or minimizing power consumption of a subcutaneously implantable sensor device and/or extending its useful life is provided. Such a method may generally include controlling activation and deactivation of a communications module, and in some aspects, other modules of the implantable sensor device. In some aspects, control of such device components may be implemented by the techniques and methods recited herein, such as by detection of the presence/absence, or of a specific concentration of a predetermined chemical agent.

In addition to the method of reducing and/or minimizing power consumption of the subcutaneously implantable sensor device, and thus extending its useful service life, the process of controlling activation and deactivation of the communications module further provides other advantages, such as security advantages. In one aspect, the securing of the data and information collected by the sensor can be increased or maximized by exercising control over the timing and duration of operation of the communications module in the implantable sensor device.

Security of the collected data and/or information to be transmitted to or from the implantable sensor device can be further increased by implementing the use of security codes or authentication codes or protocols between the implantable sensor device and the remote device. The logic and implementation of these types of security or privacy measures is well known generally and any specific type of program logic in the implantable sensor device and/or the remote device may be used, such as security codes, etc. In one embodiment, upon making an initial connection, the implantable sensor device and remote device exchange a user authorization code, access verification code, security code, or the like to confirm the permission of the communication session between the devices. In some embodiments, the authorization may be made by a user inputting a pin number or password into the remote device at a point when prompted following establishment of a communication connection between the devices. When the information input by the user on the remote device is recognized or otherwise accepted by the implantable sensor device, then the communication session may proceed.

The predetermined chemical agent can be nearly any agent, of either exogenous or endogenous origins. As previously mentioned, in some aspects, an analyte can be the predetermined chemical agent. This is particularly true when the analyte is an endogenous agent or substance. A number of mechanisms may be used to administer a predetermined chemical agent to the subject for purposes of activating the communications module and/or other functions or operations of the implantable sensor device, once it is implanted inside a subject. Nearly any acceptable mechanism for administering the predetermined chemical agent capable of introducing it (or a specified derivative thereof, such as a metabolite formed inside the body) at the implantable sensor device can be used. Examples of mechanisms of administering the predetermined chemical agent include without limitation, inhalation of the agent, transdermal absorption of the agent, ingestion of the agent (i.e. orally), injection of the agent, etc.

In one aspect, the predetermined chemical agent can be intentionally administered to the subject in order to activate communication with the implantable sensor device. This can occur either by introducing the predetermined chemical agent without regard to a concentration achieve, or by introducing the predetermined chemical agent in an amount sufficient to achieve a specific concentration thereof at the implantable sensor device. As previously recited, the implantable sensor device can be programmed to control the communications module and/or other components based on either the presence or absence of a predetermined chemical agent, or upon detecting the predetermined chemical agent in specific concentration.

The flexibility afforded in how the communication module and/or functions of the implantable sensor are controlled provides an opportunity to gather data from a group of subjects at the same time and location. In one example, subjects enrolled in a clinical trial or study of a new pharmacotherapy or other testing or monitoring program can each have implanted one or more implantable sensor devices of the type and nature described. The sensor can collect data desired to be monitored, such as for example, dosing of a drug being tested, amounts and concentrations achieved, duration of activity, etc. When data reporting is desired, rather than take blood samples or perform other tests on the individual subjects, an entire group of subjects may be assembled and data collected all at once. In this way the information that has been collected by the implantable sensor device over a period of time can be reported. A wide number of applications of this type may be employed, for example, monitoring subjects for alcohol or drug consumption over time as part of a program, such as a study or compliance program, monitoring aspects of a subject's diet or exercise habits as part of a training routine, or monitoring a subject's bodily functions, such as insulin productions and levels, blood sugar levels, or other content, such as enzyme, protein, or oxygen levels can be monitored among others.

In some embodiments, the predetermined chemical agent (i.e. which controls the communications module) can be an analyte which the implantable sensor device is configured to detect. In such case, upon detection of the analyte, the implantable sensor device can initiate a signal or communications activity. In this way, the implantable sensor device is effectively capable of monitoring the subject's in-vivo environment and then causing an action upon detection of the analyte. In one embodiment, this ability can further translate to an ability to monitor external environmental conditions of the subject. For example, if the subject encounters a dangerous or undesirable gas in its surrounding atmosphere, the sensor can detect such gas as it is inhaled by the subject. Upon detection of such gas the sensor can initiate a signal to the user, such as the heat, sound, electrical shock, or vibration signal, or the communications module can be activated and communication with a remote device can be initiated. Such actions can alert the subject, or another individual or system monitoring the subject as to the presence of the analyte and hence any danger or benefit to the subject.

In another example, the activation of the communications system in the implantable sensor device can cause the remote device, or a second remote device in communication with the remote device, to perform a function. For example, if the implantable sensor device is configured to monitor a subject's blood sugar, then upon detecting a specified blood sugar level, the communications module of the implantable sensor device can be activated and communication such information to the remote device. The remote device then can communicate with the second remote device, for example, and insulin pump worn by the subject and control the administration of insulin to the subject. In some embodiments, the remote device may be the insulin pump itself and the act of controlling insulin administration carried out without the need for a second remote device. Accordingly, in some invention embodiments, a method for administering a therapeutic or beneficial agent to a subject can include, monitoring an analyte in the subject using an implantable sensor device as recited herein, activating a communications module of the implantable sensor device upon detection of the analyte, including presence or amount thereof, and communicating information from the implantable sensor device to a remote device which either direction or indirectly performs a function that results in administration of a therapeutic or beneficial agent to the subject. In some aspects, the remote device may directly perform the function of administering the therapeutic or beneficial agent. In other aspects, the remote device may communicate with a second remote device that performs the administration.

In one embodiment, the remote device can administer a specified dose or amount of the therapeutic or beneficial agent. In another embodiment, the administration of the therapeutic or beneficial agent can continue until the remote device (or second remote device) receives a communication from the implantable sensor device indicating that administration should stop. For example, when the implantable sensor device detects the presence of the therapeutic or beneficial agent, including a certain amount or concentration thereof, the communications module of the device can be activated, if it is inactive, and this information can be communicated to the remote device. Upon receipt of the information by the remote device, the administration of the therapeutic or beneficial agent can be terminated, or otherwise reduced or controlled. Likewise, such activity can take place not only upon detection of the therapeutic or beneficial agent by the implantable sensor device, but also upon detection of an absence of the analyte that initiated the administration activity.

As previously mentioned, the predetermined chemical agent can be used to either activate or deactivate the communications module. For example, upon detection of the predetermined chemical agent the communication module can be activated for a predetermined period of time, or deactivated upon the expiration of a predetermined period of time. Alternatively, the communication module could be activated by at least one of the presence, absence, increase in concentration, or decrease in concentration of the predetermined chemical agent, or analyte which may be the predetermined chemical agent. The communication module and/or other device functions or operations could additionally be deactivated or otherwise controlled by the detection of a second predetermined chemical agent. For example, the communications module could be activated upon detection of an exogenous analyte, which is also the predetermined chemical agent, and begin transmitting data collected by the sensor device until a second predetermined chemical agent is administered to the individual in whom the sensor device is implanted and the second predetermined chemical agent is detected by the sensor device, at which time the communication module can return to a deactivated state.

Figure 4:
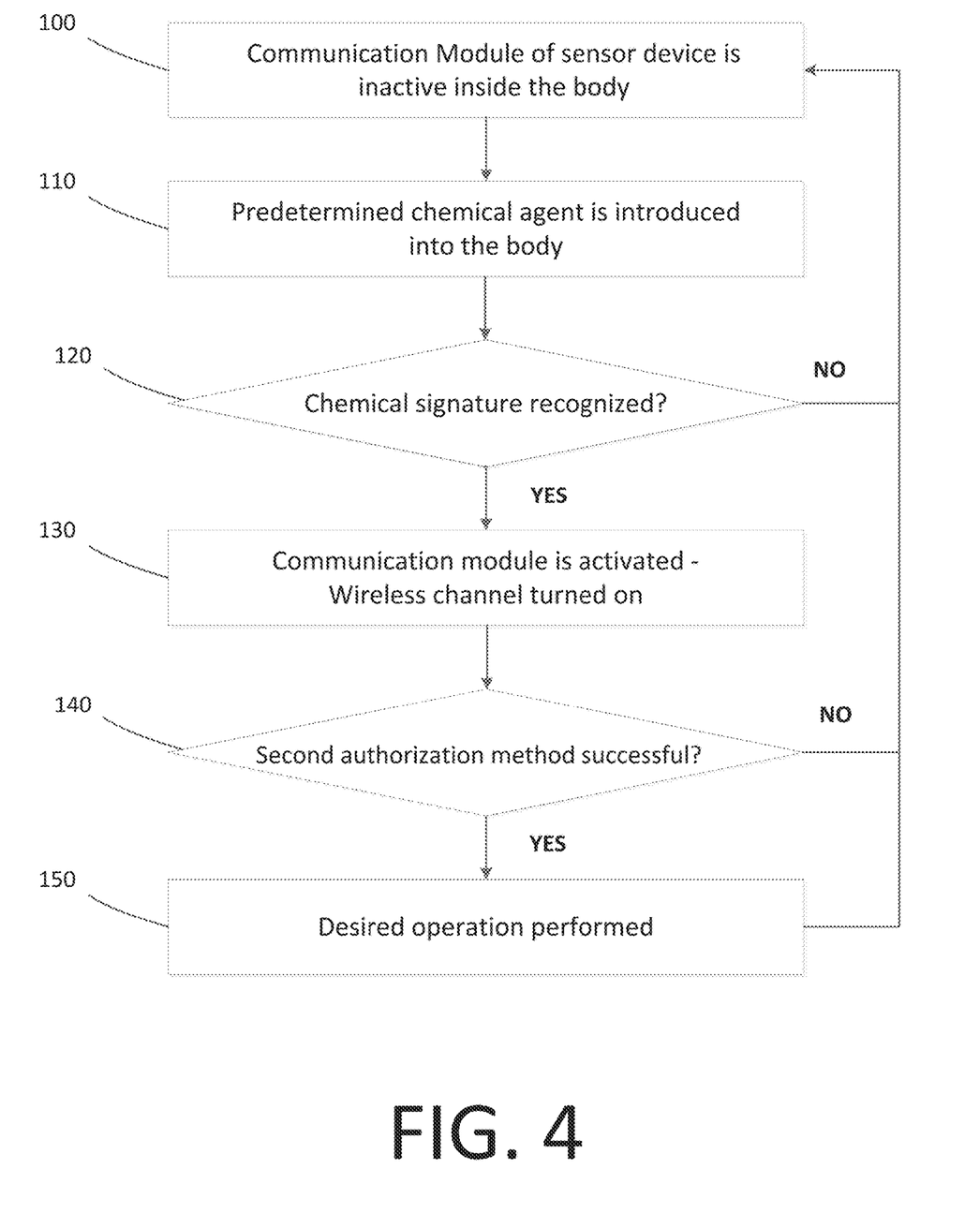
FIG. 4 is a flow chart depicting a method of operating a subcutaneously implantable sensor device in accordance with an invention embodiment.

Referring to FIG. 4 is shown an example of an embodiment of activating and deactivating the communications module of a subcutaneously implanted sensor device in accordance with one invention embodiment. As shown, the communication module of the sensor device implanted in a subject is found in an inactive state 100. A predetermined chemical agent is introduced into the subject's body 110. If the chemical signature is recognized 120, the communication module is activated and a wireless channel is turned on 130. Otherwise, the communication module remains inactive 100. Once the communication module is activated and a wireless channel is turned on 130, a second authorization method, such as a passkey, can also be employed or otherwise required 140. If the passkey is successful, the desired operation of the communication module is performed 150, otherwise the communication module will return to an inactive state 100.

Another embodiment of the present technology is directed toward a method of reporting collected sensor data from a subcutaneously implantable sensor device as previously described herein. This method involves activating a communication module of the sensor device upon detection of a predetermined chemical agent by the chemical sensor of the sensor device and transmitting data collected by a data collection module of the sensor device to a remote device.

As previously described, the predetermined chemical agent can be inhaled, transdermally absorbed, ingested, injected or otherwise delivered to an individual in whom the sensor device is implanted. This can be done by providing an inhalable formulation, a topically administered formulation, an orally administered formulation, or injectable formation, or the predetermined chemical agent could otherwise come from the surroundings of the person in whom the sensor device is implanted. Alternatively, the predetermined chemical agent could be a metabolite of an agent similarly administered or obtained from the individual's surroundings.

To reiterate, the predetermined chemical agent can be used to either activate or deactivate the communications module. For example, upon detection of the predetermined chemical agent the communication module can be activated for a predetermined period of time, or deactivated upon the expiration of a predetermined period of time. Alternatively, the communication module could be activated by at least one of the presence, absence, increase in concentration, and decrease in concentration of an analyte, which may be the predetermined chemical agent. The device could then be deactivated by at least one of the presence, absence, increase in concentration, and decrease in concentration of an analyte, which may be the predetermined chemical agent or a second predetermined chemical agent. Additionally, the communication module could require a second-factor for authentication. Once the communication module is activated, it could also be deactivated by a user. Deactivation of the communication module can also minimize power usage of the sensor device. In one aspect of this embodiment, activation of the communication module also results in a wireless channel being turned on.

To further reiterate, the remote device can perform an action based on the data received, such as report the data to a user, administer an agent to an individual in whom the sensor device is implanted, provide an electrical stimulus, or signal a result, such as an alarm indicator. The alarm indicator signal can be at least one of vibrational, thermal, optical, auditory, olfactory, electrical, chemical and biochemical. The remote device can also transmit the data to a remote database.

In yet another invention embodiment, a method of reporting collected sensor data from a population of subcutaneously implantable sensor devices as previously described herein is provided. Such a method involves can include programming controller modules of a first group of sensor devices within the population with program logic that controls communication modules of the first group of sensor devices based upon detection of a first predetermined chemical agent by the sensors of the sensor devices. Additionally, controller modules of a second group of sensor devices within the population can be programmed with program logic that controls communication modules of the second group of sensor devices based upon detection of a second predetermined chemical agent by the sensors of the sensor devices. The sensor data collected from each group within the population is then transmitted to a remote device. This can allow data to be transmitted from one group of people based on a predetermined chemical key, while maintaining the privacy and data security of the another group of people whose implantable devices use an different chemical key.

The first and second predetermined chemical agents can be inhaled, transdermally absorbed, ingested, injected or otherwise delivered to an individual in whom the sensor device is implanted. This can be done by providing an inhalable formulation, a topically administered formulation, an orally administered formulation, or injectable formation, or the predetermined chemical agent could otherwise come from the surroundings of the person in whom the sensor device is implanted. Alternatively, at least one of the first and second predetermined chemical agents could be a metabolite of an agent similarly administered or obtained from the individual's surroundings.

The first and second predetermined chemical agents can be used to either activate or deactivate the communication modules of the first and second groups of sensor devices, respectively. For example, the first predetermined chemical agent could be administered to both individuals in whom the first group of sensor devices are implanted and individuals in whom the second group of sensor devices are implanted, but only the communication modules of the first group of sensor devices will be activated and the communication modules of the second group of sensor devices will remain inactive. The communication modules of the first group of sensor devices could remain active until the concentration of the first predetermined chemical agent is reduced below a specified level. Once the communication modules of the first and second groups of sensor devices are activated, they could also be deactivated by a user. Deactivation of the communication modules of the first and second group of sensor devices can also minimize power usage among those sensor devices. In one aspect of this embodiment, activation of the communication modules of the first and second groups of sensor devices also results in a wireless channel being turned on in those sensor devices. Once the communication modules in at least one of the first and second group of sensor devices is activated, the data collected by the respective data collection modules can be transmitted to a remote device(s).

The remote device can perform an action based on the data received, such as report the data to a user, administer an agent to an individual in whom the sensor device is implanted, provide an electrical stimulus, or signal a result, such as an alarm indicator. The alarm indicator signal can be at least one of vibrational, thermal, optical, auditory, olfactory, electrical, chemical, and biochemical. The remote device can also transmit the data to a remote database.

Another invention embodiment provides a biological sensing and reporting system comprising an implantable subcutaneous sensor device and a remote device configured to receive data transmitted from the sensor device.

In an exemplary embodiment, a subcutaneously implantable sensor device may comprise: a housing; at least one sensor; a power module configured to power the sensor device; a data collection module configured to collect and store sensor data; a communication module configured to communicate with a remote device; and a controller module configured to control operation of the sensor device, wherein the controller module controls the communication module based upon detection of a predetermined chemical agent by the at least one sensor.

In one example, a subcutaneously implantable sensor device can include:
- a housing having substantially opposing sides;
- at least one chemical sensor on one of the opposing sides;
- a power module configured to power the sensor device;
- a data collection module configured to collect and store sensor data;
- a communication module configured to wirelessly communicate with a remote device; and
- a controller module configured to control operation of the sensor device and equipped with program logic that controls the communication module based upon detection of a predetermined chemical agent or an analyte by the at least one chemical sensor.

In one example, the at least one chemical sensor has a plurality of recognition sites.

In one example, the plurality of recognition sites can be configured to detect a plurality of predetermined chemical agents or analytes.

In one example, the at least one chemical sensor is an array of sensors.

In one example, the array of sensors is configured to detect a plurality of predetermined chemical agents or analytes.

In one example, the sensor device can also include at least one sensor or an array of sensors on each of the opposing sides of the housing.

In one example, the at least one chemical sensor is of a type selected from the group of: electrochemical, potentiometric, amperometric, conductometric, chemicapacitive, chemiresistive, photoionizing, field-effect transistor, physical transducer, optical transducer, biochemical, affinity-based, thermochemical, optical, and piezoelectric type sensors.

In one example, the at least one chemical sensor is configured to detect at least one of the presence, absence, or a concentration of the predetermined chemical agent or analyte.

In one example, the controller module is configured to activate the communication module upon detection of the presence, absence, or concentration of the predetermined chemical agent or analyte.

In one example, the controller module is configured to deactivate the communication module upon detection of the presence, absence, or concentration of the predetermined chemical agent or analyte.

In one example, the analyte is the predetermined chemical agent.

In one example, the sensor device is further configured to provide a biofeedback signal to a subject in whom the sensor device is implanted upon detection of a predetermined chemical agent or an analyte.

In one example, the analyte is the predetermined chemical agent.

In one example, the biofeedback signal is at least one of vibrational, thermal, optical, auditory, olfactory, electrical, chemical and biochemical.

In one example, the sensor device can also include a component that provides for release of an agent stored within the sensor device.

In one example, the biofeedback signal prompts release of an agent from the sensor device, or release of an endogenous agent within the individual in which the sensor device is implanted.

In one example, a biological data sensing and reporting system can include;
- an implantable subcutaneous sensor device as recited previously; and
- a remote device configured to wirelessly communicate with the sensor device.

In one example, the remote device is configured to send, receive, or send and receive data to and from the sensor device.

In one example, the remote device is further configured to report the transmitted data to a user.

In one example, the remote device is further configured to receive information input from a user.

In one example, the information is transmitted from the remote device to the sensor device.

In one example, the information sent from the remote device to the sensor device controls an operation of the sensor device.

In one example, the operation is operation of the data collection module.

In one example, operation of the data collection module includes at least one of initiation of data collection, termination of data collection and deletion of stored data.

In one example, the remote device further comprises components for administration of an agent to the subject in which the sensor device is implanted.

In one example, the remote device is configured to administer an agent to the subject upon receiving information from the sensor device.

In one example, the remote device is further configured to signal a result.

In one example, the signal is an alarm indicator.

In one example, the remote device is a hand held device.

In one example, the hand held device is a smart device.

In one example, the remote device is configured to transmit data to a second remote device.

In one example, the second remote device includes remote database.

In one example, the second remote device is configured to administer an agent to the subject in response to the data received.

In one example, a method of controlling communication activity of a subcutaneously implantable sensor device can include:
- identifying a predetermined chemical agent to be detected by a sensor; and
- activating a communications module of the subcutaneously implantable sensor device in response to detection of the predetermined chemical agent.

In one example, activating the communications module further comprising programming a controller module of the sensor device with logic that controls operation of a communication module of the sensor device based upon detection of the predetermined chemical agent.

In one example, the predetermined chemical agent is inhaled by a subject in which the sensor device is implanted.

In one example, the predetermined chemical agent is provided by an inhalable formulation.

In one example, the predetermined chemical agent is absorbed transdermally by a subject in which the sensor device is implanted.

In one example, the predetermined chemical agent is provided by a topically administered formulation.

In one example, the predetermined chemical agent is injested by an individual in which the sensor device is implanted.

In one example, the predetermined chemical agent is provided by an orally administered formulation.

In one example, the predetermined chemical agent is injected into an individual in which the sensor device is implanted.

In one example, the predetermined chemical agent is a metabolite of an agent delivered to an individual in which the sensor device is implanted.

In one example, the communication module is activated for a predetermined period of time.

In one example, the communication module is deactivated by expiration of a predetermined period of time.

In one example, the communication module is activated or deactivated by the presence or absence of a predetermined chemical agent or an analyte.

In one example, the analyte is the predetermined chemical agent.

In one example, the communication module is activated or deactivated by an increase or reduction in concentration of a predetermined chemical agent or an analyte.

In one example, the analyte is the predetermined chemical agent.

In one example, deactivation of the communication module minimizes power usage.

In one example, a method of reporting collected sensor data from a subcutaneously implantable sensor device, as recited previously, can include:
 activating a communication module of the sensor device upon detection of a predetermined chemical agent by a chemical sensor of the sensor device; and
 transmitting data collected by a data collection module of the sensor device to a remote device.

In one example, the predetermined chemical agent is inhaled by an individual in which the sensor device is implanted.

In one example, the predetermined chemical agent is provided by an inhalably administered formulation.

In one example, the predetermined chemical agent is absorbed transdermally by an individual in which the sensor device is implanted.

In one example, the predetermined chemical agent is provided by a topically administered formulation.

In one example, the predetermined chemical agent is injested by an individual in which the sensor device is implanted.

In one example, the predetermined chemical agent is provided by an orally administered formulation.

In one example, the predetermined chemical agent is injected into an individual in which the sensor device is implanted.

In one example, the predetermined chemical agent is a metabolite of an agent delivered to an individual in which the sensor device is implanted.

In one example, the communication module is activated for a predetermined period of time.

In one example, the communication module is deactivated by expiration of a predetermined period of time.

In one example, the communication module is activated or deactivated by the presence or absence of a predetermined chemical agent or an analyte.

In one example, the analyte is the predetermined chemical agent.

In one example, the communication module is activated or deactivated by an increase or reduction in concentration of a predetermined chemical agent or an analyte.

In one example, the analyte is the predetermined chemical agent.

In one example, deactivation of the communication module reduces power usage.

In one example, detection of the predetermined chemical agent activates a second-factor for authentication by a user.

In one example, the remote device administers an agent to the subject upon receiving information from the sensor device.

In one example, the remote device reports the data to a user.

In one example, the remote device provides an electrical stimulus.

In one example, the remote device signals a result.

In one example, the signal is an alarm indicator.

In one example, the alarm indicator signal is at least one of vibrational, thermal, optical, auditory, olfactory, electrical, chemical and biochemical.

In one example, the remote device transmits the data to a second remote device.

In one example, the second remote device includes a remote database.

In one example, the transmission of data is wireless.

In one example, the wireless transmission is performed via at least one of Bluetooth, Wi-Fi, WiMAX, IEEE 802.11, cellular, radio, electromagnetic and optical communication.

In one example, a method of reporting sensor data from a subcutaneously implantable sensor device can comprise:
 activating a communication module of the sensor device upon detection of a predetermined chemical agent by a chemical sensor of the sensor device; and
 transmitting sensor data collected by a data collection module of the sensor device to a remote device.

In one example, the predetermined chemical agent is inhaled by a subject in which the sensor device is implanted.

In one example, the predetermined chemical agent is provided by an inhalably administered formulation.

In one example, the predetermined chemical agent is absorbed transdermally by a subject in which the sensor device is implanted.

In one example, the predetermined chemical agent is provided by a topically administered formulation.

In one example, the predetermined chemical agent is ingested by a subject in which the sensor device is implanted.

In one example, the predetermined chemical agent is provided by an orally administered formulation.

In one example, the predetermined chemical agent is injected into a subject in which the sensor device is implanted.

In one example, the predetermined chemical agent is a metabolite of an agent delivered to a subject in which the sensor device is implanted.

In one example, the communication module is activated for a predetermined period of time.

In one example, the communication module is deactivated by expiration of a predetermined period of time.

In one example, the communication module is activated or deactivated by the presence or absence of a predetermined chemical agent or an analyte.

In one example, the analyte is the predetermined chemical agent.

In one example, the communication module is activated or deactivated by an increase or reduction in concentration of a predetermined chemical agent or an analyte.

In one example, the analyte is the predetermined chemical agent.

In one example, deactivation of the communication module reduces power usage and extends an effective operative lifetime of the implantable sensor device.

In one example, the remote device and/or the implantable sensor device include program logic requiring an authentication mechanism following initial communication between the devices.

In one example, the authentication is input into the remote device by a user of the remote device.

In one example, the authentication is a pin number, a password, or biometric data.

In one example, the remote device reports the transmitted data to a user.

In one example, the remote device signals a result.

In one example, the signal is an alarm indicator.

In one example, the alarm indicator signal is at least one of vibrational, thermal, optical, auditory, olfactory, electrical, chemical and biochemical.

In one example, the remote device transmits the data to a second remote device.

In one example, the second remote device includes a remote database.

In one example, the transmission of data is wireless.

In one example, the wireless transmission is performed via at least one of Bluetooth, Wi-Fi, WiMAX, IEEE 802.11, cellular, radio, electromagnetic and optical communication.

In one example, the subcutaneously implantable sensor device is a plurality of subcutaneously implantable sensor devices either in a single subject, or in a plurality of subjects.

In one example, the plurality of subjects is divided into specific groups.

In one example, the subcutaneously implantable sensor devices of each group are activated by different predetermined chemical agents than other groups, or wherein the subcutaneously implantable sensors of each group are activated by different concentrations of a predetermined chemical agent than other groups.

In one example, an invention embodiment includes a method of administering a therapeutic agent to a subject in need thereof and includes:
collecting data about an analyte in the subject with a subcutaneously implantable sensor device;
activating a communication module of the sensor device upon detection of a predetermined chemical agent by a chemical sensor of the device;
transmitting the collected data to a remote device;
determining the subject's need based upon the data;
selecting a therapeutic agent, an amount of a therapeutic agent to be administered to the subject; and
administering the therapeutic agent to the subject.

In one example, the predetermined chemical agent is the analyte.

In one example, the remote device administers the therapeutic agent to the subject.

In one example, the remote device communicates with a second remote device which administers the therapeutic agent to the subject.

While the forgoing examples are illustrative of the specific embodiments in one or to more particular applications, it will be apparent to those of ordinary skill in the art that numerous modifications in form, usage and details of implementation can be made without departing from the principles and concepts articulated herein. Accordingly, no limitation is intended except as by the claims set forth below.

What is claimed is:

1. An apparatus, comprising:
a substrate comprising a corrosion-free metal or polymeric material;
at least one sensor disposed on a surface of the substrate to detect or measure one or more analytes in a human body, wherein the at least one sensor comprises an electrochemical sensor;
a communication circuitry disposed inside the substrate and coupled with the at least one sensor, to wirelessly communicate data that corresponds to the detection or measurements of the one or more analytes to a remote device;
a controller circuitry disposed inside the substrate and coupled with the at least one sensor and the communication circuitry, to control operation of the at least one sensor and the communication circuitry, including collection of data associated with the detection or measurements of the one or more analytes, and transmission of the collected data to the remote device; and
a power source disposed inside the substrate, to power the apparatus,
wherein the apparatus is implantable in the human body.

2. The apparatus of claim 1, wherein the power source comprises a battery or an inductive component to receive power from a remote device.

3. The apparatus of claim 1, wherein the at least one sensor comprises an array of sensors.

4. The apparatus of claim 1, further comprising a data collection device coupled with the sensor, to collect and store the data.

5. The apparatus of claim 1, wherein the controller circuitry is to detect a signal from the at least one sensor and perform an analysis of the detected signal.

6. The apparatus of claim 1, wherein the corrosion-free metal includes one of: gold or silver.

7. The apparatus of claim 1, wherein the controller circuitry is to determine a concentration of the one or more analytes in the human body.

8. A method, comprising:
causing, by a controller circuitry disposed inside a substrate of an apparatus and powered by a power source disposed inside the substrate, to collect data corresponding to detecting or measuring, by at least one sensor disposed on a surface of the substrate of the apparatus, one or more analytes in a human body, the at least one sensor comprising an electrochemical sensor and the substrate comprising a corrosion-free metal or polymeric material; and
causing, by a controller circuitry powered by the power source, the collected data to be wirelessly transmitted, by a communication circuitry disposed inside the substrate of the apparatus, to a remote device.

9. The method of claim 8, further comprising:
detecting, by the controller circuitry, a signal from the at least one sensor; and
performing, by the controller circuitry, an analysis of the detected signal, wherein the signal indicates the detection or measurements of the one or more analytes.

10. The method of claim 8, further comprising: causing, by the controller circuitry, the data to be stored.

11. The method of claim 8, further comprising: determining, by the controller circuitry, a concentration of the one or more analytes in the human body.

12. The method of claim 8, wherein the corrosion-free metal includes one of: gold or silver.

13. The method of claim 8, wherein the at least one sensor comprises an array of sensors.

* * * * *